US005953776A

United States Patent [19]
Sanders et al.

[11] Patent Number: 5,953,776
[45] Date of Patent: Sep. 21, 1999

[54] MEDICAL APPARATUS INCLUDING A PATIENT TABLE WITH A COMPACT AND RIGID ELEVATING MECHANISM

[75] Inventors: Leonardus C. M. Sanders; Johannes H. A. Van De Rijdt; Johan W. Rust, all of Eindhoven, Netherlands

[73] Assignee: U.S. Philips Corporation, New York, N.Y.

[21] Appl. No.: 08/990,869

[22] Filed: Dec. 15, 1997

[30] Foreign Application Priority Data

Dec. 20, 1996 [EP] European Pat. Off. .............. 96203650

[51] Int. Cl.⁶ .................................................. A61G 7/012
[52] U.S. Cl. .................................... 5/611; 5/11; 378/209; 108/145
[58] Field of Search .......................... 5/11, 611; 108/145, 108/147; 378/177, 209

[56] References Cited

U.S. PATENT DOCUMENTS

| | | | |
|---|---|---|---|
| 3,203,670 | 8/1965 | Farris | 108/147 |
| 3,237,921 | 3/1966 | Jay | 108/47 X |
| 3,253,817 | 5/1966 | Lauterbach | 5/611 X |
| 3,797,819 | 3/1974 | Platz et al. | 269/322 |
| 4,157,743 | 6/1979 | Masuda et al. | 182/141 |
| 4,449,262 | 5/1984 | Jahsman et al. | 5/611 X |
| 4,451,945 | 6/1984 | Heinz et al. | 5/611 |
| 5,694,864 | 12/1997 | Langewellpott | 108/145 |

*Primary Examiner*—Michael F. Trettel
*Attorney, Agent, or Firm*—Dwight H. Renfrew, Jr.

[57] ABSTRACT

One requirement imposed on a patient table is that it may occupy only a small floor surface area. Therefore, a patient table having a compact base is required. For a variety of applications, moreover, it is desired that the table is also constructed to be very rigid in the direction of adjustment of its height. To this end, the height adjustment system supporting the table is provided with a drive mechanism which consists of two mutually parallel threaded spindles (54, 56) which pass through an associated nut (50, 52) and expand in two mutually opposed directions. The two threaded spindles are preferably driven by a single motor (70). In order to achieve adequate rigidity in the horizontal direction, the hinge is constructed so as to comprise two arms (28, 30) only.

20 Claims, 5 Drawing Sheets

MEDICAL APPARATUS INCLUDING A PATIENT TABLE WITH A COMPACT AND RIGID ELEVATING MECHANISM

BACKGROUND OF THE INVENTION

1. Field of the Invention

The invention relates to an apparatus for medical diagnosis and/or therapy, including a patient table provided with a patient table top, an elevating mechanism for adjusting the height of the table top, said elevating mechanism being provided with at least one hinge which supports the patient table top, bears on a base surface and comprises at least two arms, and a drive mechanism which is arranged between the base surface and the table top in order to drive the height adjustment of the elevating mechanism.

2. Description of the Related Art

An apparatus comprising a table top and an elevating mechanism for adjusting the height of the table top is known from U.S. Pat. No. 4,157,743.

In apparatus for medical applications utilizing a patient table, the height of the patient table is preferably adjustable between a lowermost position comparatively close to the floor of the workspace and an uppermost position comparatively far above this floor. In order to achieve a comparatively low lowermost position of the patient table it would be feasible to form a recess in the floor of the workspace in order to lower the elevating mechanism therein. However, building managers do not appreciate interventions in the building structure in order to accommodate apparatus; moreover in most buildings it is not possible to lower an apparatus (partly) into the floor because the floor of one space at the same time constitutes the ceiling of a space situated therebelow. Therefore, there is a need for an elevating mechanism which has a small structural height in the lowermost position and a high height in the uppermost position.

A further requirement imposed on a patient table is that it should occupy a limited floor surface area only, so that the attending staff can comfortably work at and walk around the table without colliding with the frame of the table or without their movements being impeded. Consequently, a patient table having a compact base construction is required.

Furthermore, the patient table in apparatus for medical applications is increasingly required to be highly resistant to bending in load conditions, i.e. it should be constructed so as to be very rigid. This is important for radiation therapy where first a region of a patient to be irradiated is defined and subsequently the irradiation is actually performed. Between the defining of the region to be irradiated and the execution of the irradiation the patient, and hence also the table on which the patient is arranged, may not be displaced relative to the equipment except in a suitably controlled manner. During tomographic imaging the table should also retain exactly the same orientation and position during exposure, since the image will be unsharp otherwise.

It is expected that in the near future it will become possible to perform surgical operations on the basis of one or more images of the region to be treated which have been made in advance. Such methods are also known as image guided surgery. An image guided surgery system is used to show a surgeon the position of a surgical instrument in an operating region in the body of a patient. Images, such as X-ray CT or MRI images, are made of the patient prior to the operation. A position measuring system measures the position of the surgical instrument relative to the patient during the operation and a data processor calculates the position in such a prior image which corresponds to the measured position of the surgical instrument. The image formed in advance is displayed on a monitor and the actual position of the surgical instrument is reproduced therein. The surgeon can observe the image on the monitor so as to see where the surgical instrument is situated in the operating region, without the surgeon having a direct view of the instrument. The image on the monitor shows how the surgeon can move the surgical instrument in the operating region without incurring a high risk of unnecessary damaging of tissue and notably without a risk of damaging of vital organs.

Such an image guided surgery system is preferably used in neuro surgery in order to show the surgeon exactly where in the brain the surgical instrument is situated during brain surgery. During such operations it is of crucial importance that the patient is not subjected to any changes of position, other than perfectly controlled changes of position, relative to the position occupied at the instant at which the image was formed. This can be achieved only if no or only perfectly controlled movements of the table top occur.

The elevating mechanism which is known from the cited United States Patent comprises a plurality of pantographs which support the table top and each of which includes a number of pivotably interconnected arms. The known elevating mechanism occupies a surface area on the floor which is approximately equal to the dimensions of the table top to be displaced. The hinges of such an elevating mechanism can be readily constructed so as to be free from play and in order to ensure that such a hinge offers adequate rigidity against horizontal displacement, such a hinge can be constructed so as to have a width which is comparable to that of the table and also to have adequately robust hinge arms which may have, within given limits, an arbitrarily heavy construction. Using this known elevating mechanism, therefore, a base can be realized for a patient table which is sufficiently rigid and has a compact construction.

Moving the table top up and down requires a drive mechanism which fits within the compact construction of the elevating mechanism, offers adequate rigidity in the vertical direction with a view to the above rigidity requirements, and has a simple construction which preferably consists of commercially available components.

SUMMARY OF THE INVENTION

It is an object of the invention to provide an apparatus for medical diagnosis and/or therapy which includes a patient table which satisfies such requirements.

In order to achieve this object, the apparatus according to the invention is characterized in that the drive mechanism includes at least two expansion units, each of which includes a threaded spindle which passes through an associated nut, said two threaded spindles extending parallel to one another and said expansion units being arranged to expand in mutually opposed directions when driven.

Threaded spindles practically cannot be compressed under conditions of loading so that they contribute to the desired rigidity of the construction; moreover, these components are also commercially available. Because the threaded spindles are arranged to have an expanding effect in mutually opposed directions when driven, they occupy a comparatively small space only in the non-expanded state and can expand over a comparatively large distance; in the expanded state they have a length which is slightly less than three times their length in the non-expanded state.

In a preferred embodiment of the invention, the two expansion units are driven by a common drive motor.

Because each of the nuts (or each of the threaded spindles) is driven in the opposite sense, only one drive motor is required for the two expansion units; this results in an attractive embodiment from an economical point of view.

The drive mechanism is preferably arranged between the arms of the hinge. This offers a compact unit for adjustment of the height.

In another embodiment of the invention, the drive mechanism is mounted substantially halfway the hinge arms. Should the stroke of the two expansion units together be insufficient to achieve the desired height adjustment of the table, the overall height adjustment can be practically doubled by taking this step. Even though the forces acting on the threaded spindles are then higher, considering the high rigidity of these components, the overall rigidity of the table will hardly be affected.

In another embodiment of the invention the hinge arms are constructed as a parallelogram of two parallel rods. A high rigidity of the hinge construction is thus obtained, the weight of this construction nevertheless remaining comparatively low. In conditions of loading each time one of the rods is pressure-loaded whereas the other is tension-loaded. None of the two rods is additionally loaded for bending during displacement of the table in the horizontal plane, so that a high rigidity is achieved.

In another embodiment yet of the invention, the hinge consists of two arms only. Consequently, the hinge construction is very robust and compact and hence optimum, notably in combination with the above-mentioned embodiment in which the arms are formed by a parallelogram of rods.

BRIEF DESCRIPTION OF THE DRAWING

The invention will be described in detail hereinafter with reference to the Figures. Therein.

DETAILED DESCRIPTION OF THE PREFERRED EMBODIMENTS

Figure 1:
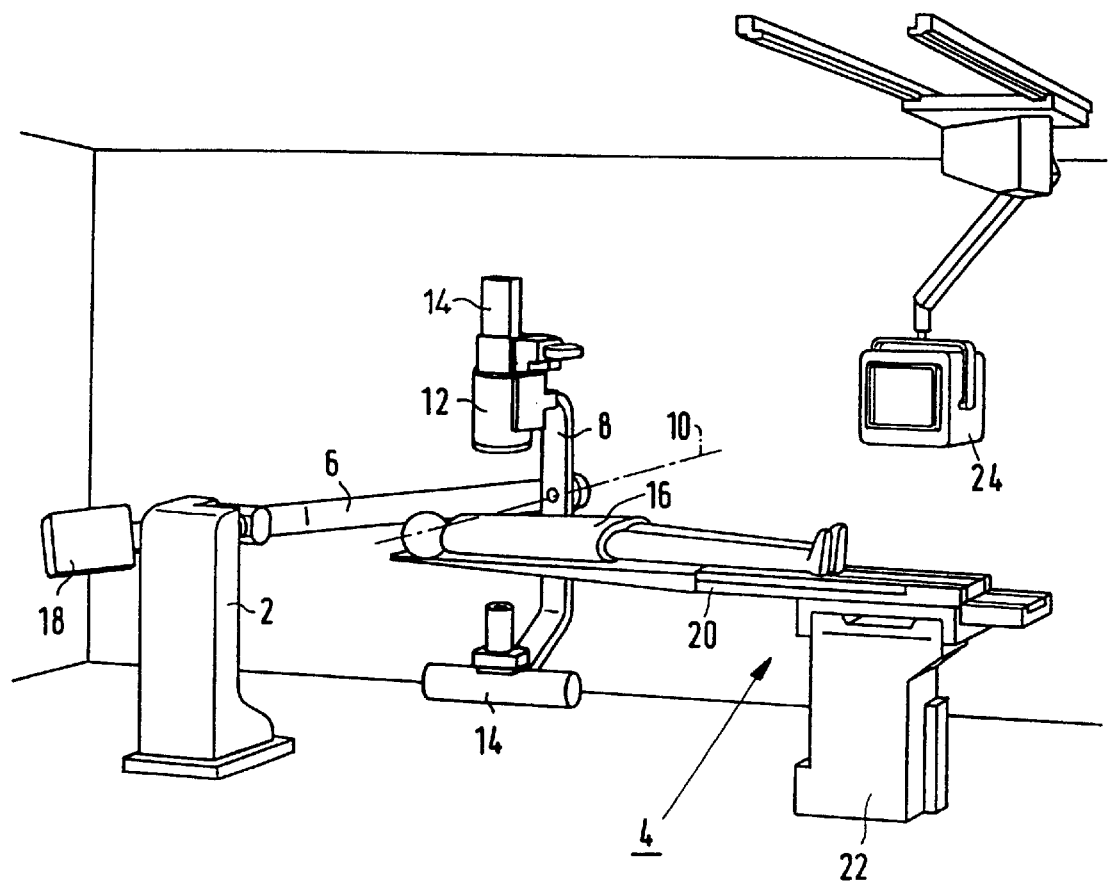
FIG. 1 is a perspective view of an apparatus for medical diagnosis and/or therapy according to the invention.

FIG. 1 is a perspective view of an apparatus for medical diagnosis and/or therapy according to the invention. The apparatus is in this case an apparatus for X-ray examinations and consists of a unit for supporting the X-ray components and a patient table 4. The unit for supporting the X-ray components includes a column 2 whereto an arm 6 is attached. The arm 6 is connected to the column 2 so as to be rotatable about two mutually perpendicular horizontal axes. To one end of the arm 6 there is attached a support 8 which is rotatable about an axis 10. The X-ray components are mounted at the ends of the support 8, i.e. an X-ray image intensifier 12 and an X-ray source 14. Under the influence of a counterweight 18, the common point of gravity of the support 8 with the X-ray components 12 and 14, the arm 6 and the counterweight 18 coincides with the point of intersection of the two horizontal, mutually perpendicular axes of rotation of the arm,6. A patient 16 is positioned on a patient table top 20 of the patient table 4. The patient table top 20 is mounted on a base 22 which is arranged on the floor of the workspace; the elevating mechanism for adjustment of the height of the table top is connected to said base as will be described hereinafter. A television monitor on which the X-ray image can be displayed is suspended from the ceiling of the workspace.

Figure 2:
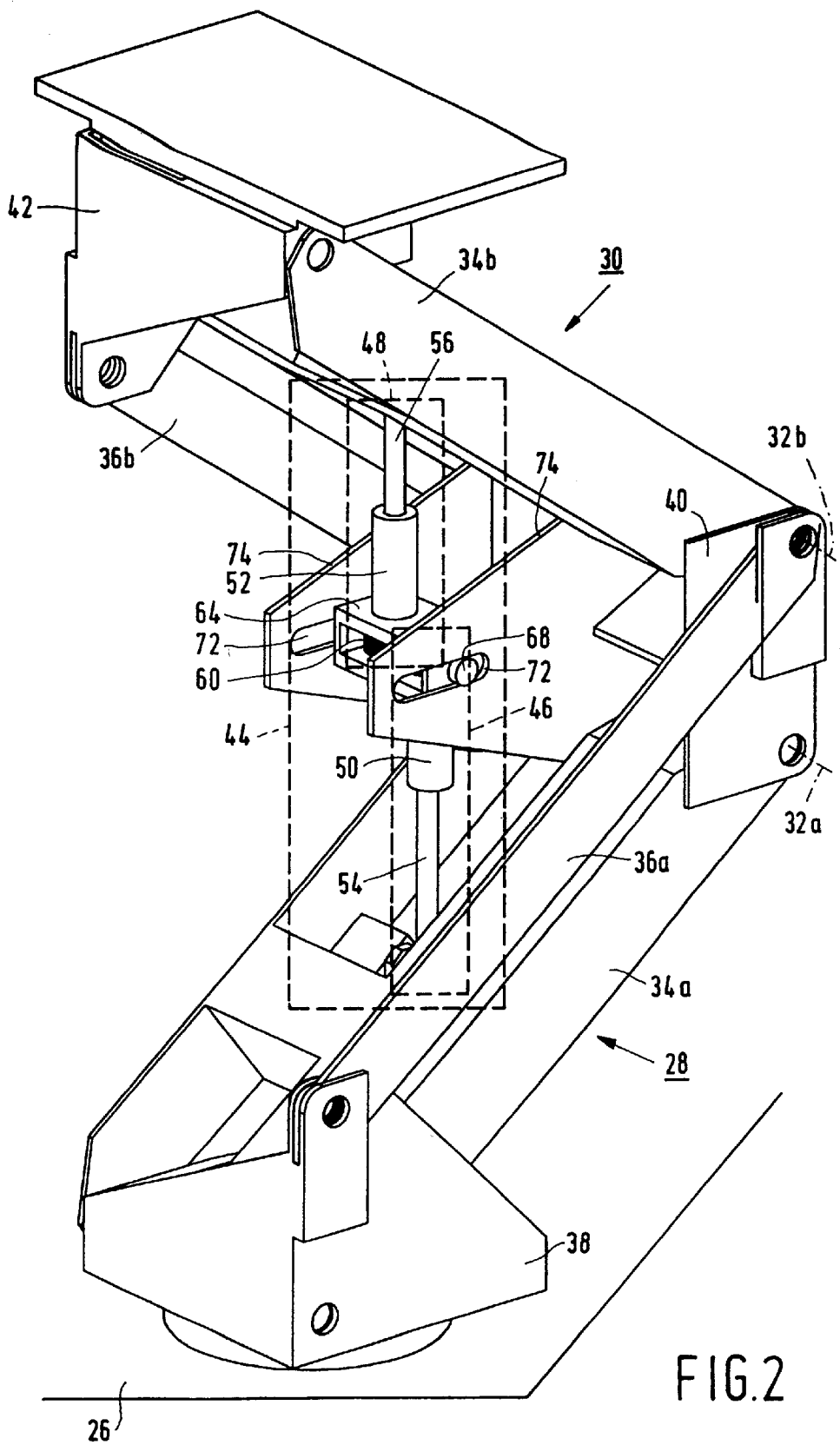
FIG. 2 is a perspective view of a part of the elevating mechanism for adjusting the height of the patient table top.
Figure 3:
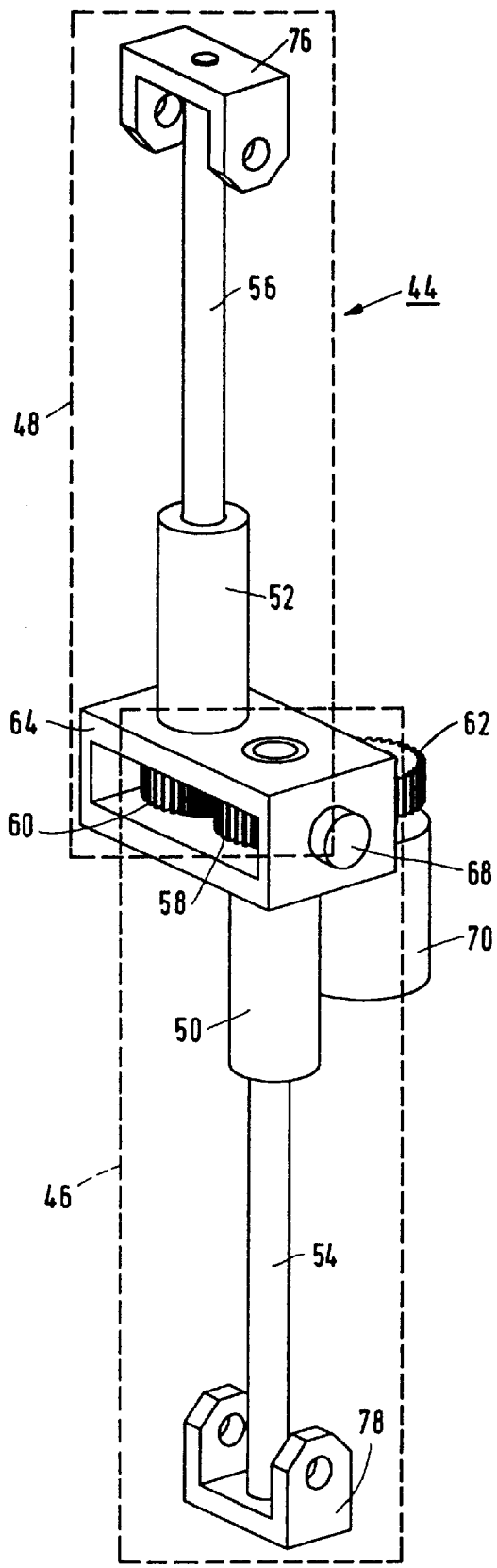
FIG. 3 is a perspective view of a drive mechanism as used in the elevating mechanism shown in FIG. 2.

The FIGS. 2 and 3 show a part of the elevating mechanism for adjusting the height of the table top 20. The part shown in FIG. 2 consists of a hinge which bears on a base surface 26 and comprises two arms 28 and 30, the arms being connected to one another so that they can hinge according to a hinge line 32. Because the arms are constructed as a parallelogram, in this embodiment there are two mutually parallel hinge lines 32a and 32b.

Each of the hinge arms 28 and 30 is constructed as a parallelogram of two parallel rods 34a, 36a and 34b, 36b, respectively. The end of the lower arm 28 which is attached to the floor 26 is mounted on a base member 38 in such a manner that the two rods 34a and 36a are secured therein in the way of a parallelogram. Furthermore, the end of the lower arm 28 which is connected to the upper arm 30 is connected to an intermediate piece 40 in such a manner that the two rods 34a and 36a are also secured therein in the way of a parallelogram. The end of the upper arm 30 which is connected to the table top 20 is connected to an end piece 42 in such a manner that the two rods 34b and 36b are secured therein in the way of a parallelogram. The end of the upper arm 30 which is connected to the 20 lower arm 28 is also connected to the intermediate piece 40 in such a manner that the two rods 34b and 36b are also secured therein in the way of a parallelogram.

Between the two arms 28 and 30 there is arranged a drive mechanism 44 which includes two expansion units 46 and 48, each of which includes a threaded spindle 54, 56 which passes through an associated nut 50, 52, respectively. The two threaded spindles 54 and 56 extend parallel to one another. The drive mechanism 44 is connected to the ends 76 and 78 (see FIG. 3) of the threaded spindles 54 and 56, halfway each of the hinge arms 28 and 30. To this end, each time one of the rods 34a and 34b, associated with each of the parallelograms 28 and 30, is constructed so as to have a H-shape, the bar of the H-shape constituting the point of support for the associated threaded spindle.

The expansion units 46 and 48 are arranged to expand in mutually opposed directions in response to driving. This is achieved in that each of the nuts 50 and 52 is provided with a gear wheel 58, 60, respectively, and also with a same type of thread (both right-handed or left-handed thread), the threaded spindles also being provided with the same thread. When the two gear wheels 58 and 60 are driven by means of a common drive motor 70, via a gear wheel of this motor, the two threaded spindles 54 and 56 are rotated in the opposite sense so that the threaded spindle 54 moves down and the threaded spindle 56 moves up or vice versa. As a result, both threaded spindles expand or contract in response to driving. The two gear wheels 58 and 60 and the motor gear wheel 62 are located so as to be rotatable in a gear wheel cluster 64. On the outside of the gear wheel cluster there are provided two projections 68 which engage a corresponding recess 72 in a guide member 74 connected to the intermediate piece 40. The combination of the projections 68 and the corresponding recesses 72 in the guide member 74 thus constitutes a mechanism for retaining the gear wheel cluster in a symmetrical position relative to the two arms 28 and 30. Consequently, the two parallelograms undergo the same displacement, so that the table top remains exactly horizontal.

FIG. 3 shows the drive mechanism 44 per se and offers a better illustration of this mechanism. The reference numerals in FIG. 3 are the same as those of the corresponding elements in FIG. 2. FIG. 3 shows the common drive motor 70 with its gear wheel 62. The Figure also shows the connection pieces 76 and 78 via which the drive mechanism 44 is secured halfway each of the hinge arms 28 and 30, i.e. on the bar of these H-shaped arms.

Figure 4:
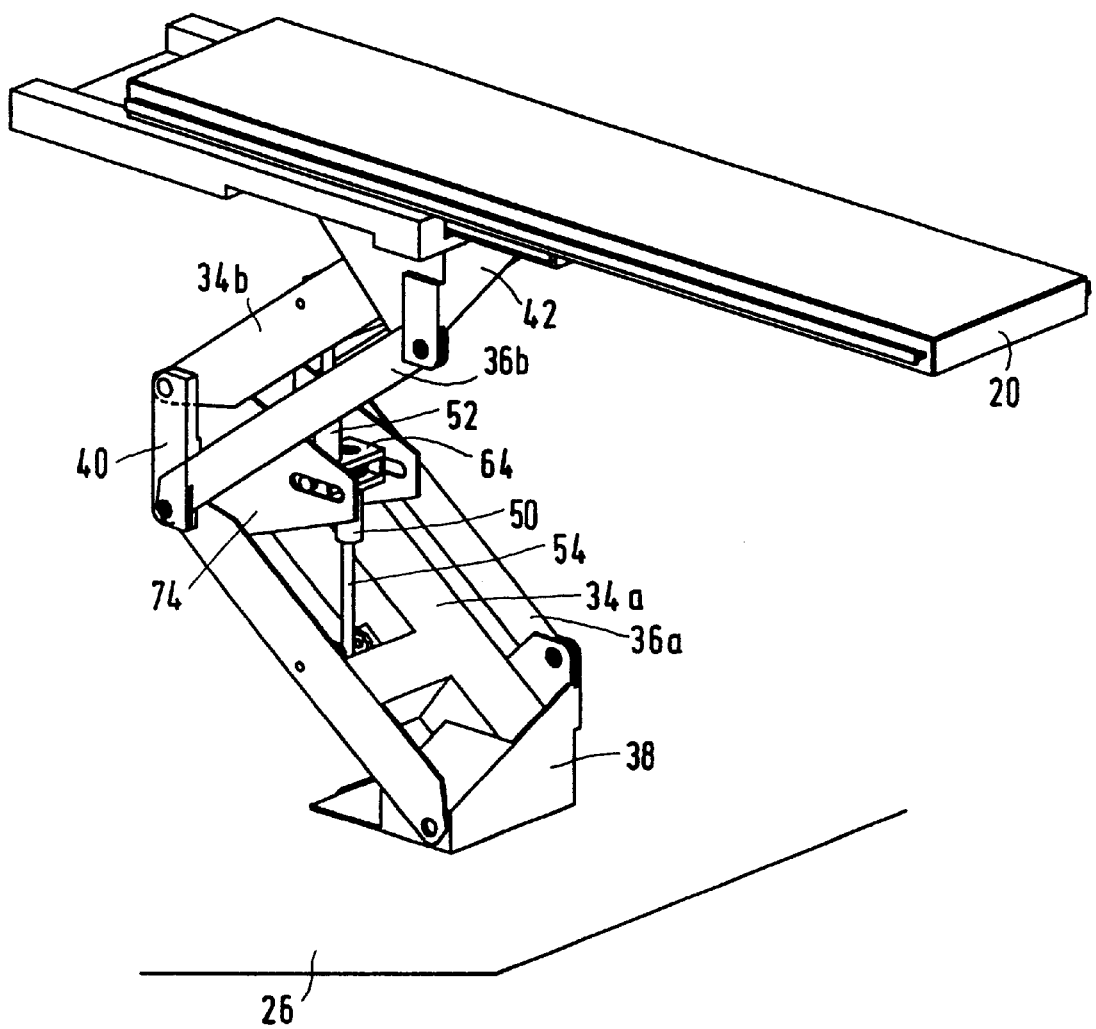
FIG. 4 is a perspective view of a patient table according to the invention in the elevated state.

FIG. 4 is a perspective view of the patient table 4 according to the invention in the elevated state. The table top 20 is mounted on the end piece 42 which is connected to the end of the upper arm 30 as described with reference to FIG. 2. The table top is moved up and down parallel to itself by rotation of the nuts 50 and 52 around the threaded spindles 54 and 56. The length of the threaded spindles is chosen so that they fit exactly in the cavity of the H-shaped rods 34a and 34b in the collapsed state.

Figure 5:
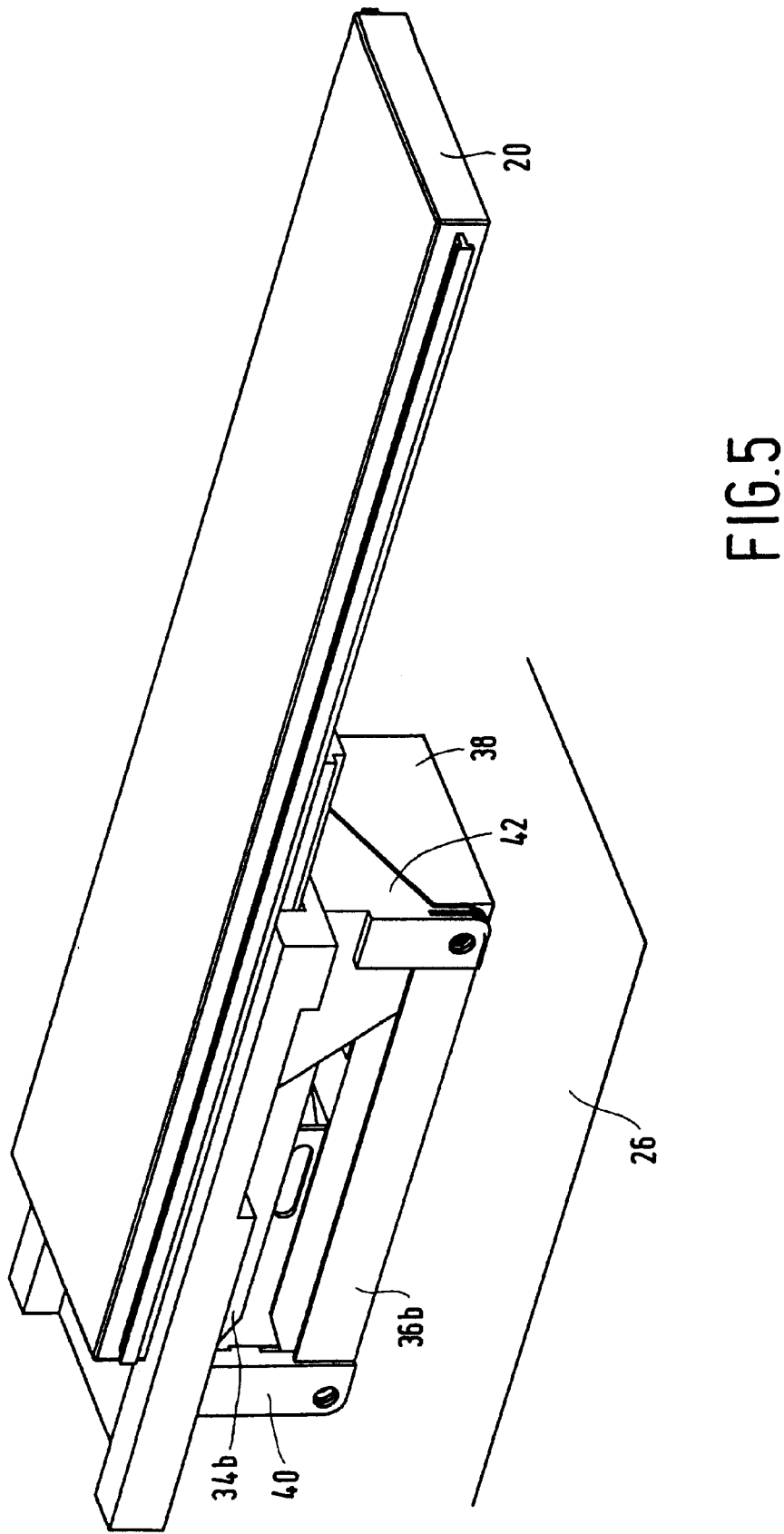
FIG. 5 is a perspective view of a patient table according to the invention in the collapsed condition.

FIG. 5 is a perspective view of the patient table 4 according to the invention in the collapsed state. The arm 34b then extends parallel to the parallelogram rod 36a and is situated to the inner side of the rod 36a. Analogously, at the other side of the elevating mechanism the arm 34a extends parallel to the parallelogram rod 36b, to the inner side of the rod 36b. Thus, in the collapsed state a very compact patient table, as is usually desired by the users of such tables, is obtained.

We claim:

1. An apparatus for medical diagnosis and/or therapy, including a patient table provided with:

a patient table top, an elevating mechanism for adjusting the height of the table top, said elevating mechanism being provided with at least one hinge which supports the patient table top, bears on a base surface and comprises at least two arms, and a drive mechanism which is arranged between the base surface and the table top in order to drive the height adjustment of the elevating mechanism, characterized in that the drive mechanism includes at least two expansion units, each of which includes a threaded spindle which passes through an associated nut, said two threaded spindles extending parallel to one another and said expansion units being arranged to expand in mutually opposite directions when driven.

2. An apparatus as claimed in claim 1, in which the two expansion units are driven by a common drive motor.

3. An apparatus as claimed in claim 1, in which the drive mechanism is arranged between the arms of the hinge.

4. An apparatus as claimed in claim 3, in which the drive mechanism is mounted substantially halfway the hinge arms.

5. An apparatus as claimed in claim 3, in which the hinge arms are constructed as a parallelogram of two parallel rods.

6. An apparatus as claimed in claim 1, in which the hinge consists of two arms only.

7. An apparatus as claimed in claim 6, in which each of the nuts engaging the threaded spindles is connected to a gear wheel, which gear wheels are accommodated together in a gear wheel cluster, there being provided a mechanism for retaining the gear wheel cluster in a symmetrical position relative to the arms.

8. An apparatus as claimed in claim 2, in which the drive mechanism is arranged between the arms of the hinge.

9. An apparatus as claimed in claim 8, in which the drive mechanism is mounted substantially halfway the hinge arms.

10. An apparatus as claimed in claim 8, in which the hinge arms are constructed as a parallelogram of two parallel rods.

11. An apparatus as claimed in claim 4, in which the hinge arms are constructed as a parallelogram of two parallel rods.

12. An apparatus as claimed in claim 9, in which the hinge arms are constructed as a parallelogram of two parallel rods.

13. An apparatus as claimed in claim 2, in which the hinge consists of two arms only.

14. An apparatus as claimed in claim 3, in which the hinge consists of two arms only.

15. An apparatus as claimed in claim 8, in which the hinge consists of two arms only.

16. An apparatus as claimed in claim 4, in which the hinge consists of two arms only.

17. An apparatus as claimed in claim 9, in which the hinge consists of two arms only.

18. An apparatus as claimed in claim 5, in which the hinge consists of two arms only.

19. An apparatus as claimed in claim 10, in which the hinge consists of two arms only.

20. An apparatus as claimed in claim 11, in which each of the nuts engaging the threaded spindles is connected to a gear wheel, which gear wheels are accommodated together in a gear wheel cluster, there being provided a mechanism for retaining the gear wheel cluster in a symmetrical position relative to the arms.

* * * * *